United States Patent [19]
Trolinder et al.

[11] Patent Number: 5,986,181
[45] Date of Patent: Nov. 16, 1999

[54] TRANSFORMATION AND REGENERATION OF FERTILE COTTON PLANTS

[75] Inventors: Norma L. Trolinder, Quanah; Jane Gay Kveton Dever, Lubbock; Linda Kay Trolinder Koonce, Idalou, all of Tex.

[73] Assignee: Southplains Biotechnologies, Inc., Lubbock, Tex.

[21] Appl. No.: 08/948,574

[22] Filed: Oct. 10, 1997

Related U.S. Application Data

[60] Provisional application No. 60/028,559, Oct. 10, 1996, and provisional application No. 60/029,493, Oct. 31, 1996.

[51] Int. Cl.$^6$ .............................. C12N 15/82; C12N 5/04; A01H 4/00; A01H 5/00
[52] U.S. Cl. .......................... 800/314; 435/468; 435/455; 800/278; 800/290; 800/295
[58] Field of Search ................................ 435/172.3, 468, 435/455; 47/410, 58; 800/205, DIG. 27, 278, 290, 295, 314

[56] References Cited

U.S. PATENT DOCUMENTS

| | | | |
|---|---|---|---|
| 5,004,863 | 4/1991 | Umbeck | 800/205 |
| 5,159,135 | 10/1992 | Umbeck | 800/205 |
| 5,846,797 | 12/1998 | Strickland . | |

FOREIGN PATENT DOCUMENTS

| | | |
|---|---|---|
| 92/15675 | 9/1992 | WIPO . |
| 97/12512 | 4/1997 | WIPO . |

OTHER PUBLICATIONS

Barrett et al. Plant Cell Tissue and Organ Culture. 1997. vol. 47: 135–144.
Carvalho et al. The EMBO Journal. 1992. vol. 11: 2595–2602.
Umbeck et al. Bio/Technology. 1987. vol. 5: 263–266.
Firoozabady and Deboer. 1993. In Vitro Cellular and Developmental Biology. vol. 29p: 166–173.
Firoozabady et al., "Transformation Of Cotton (Gossypium Hirsutum L.) by Agrogacterium Tumefaciens And Regeneration Of Transgenic Plants", *Plant Molecular Biology*, vol. 10:105–116, (1987).
Firoozabady et al., Plant Regeneration Via Somatic Embryogenesis In Many Cultivars Of Cotton (Gossypium Hirsutum L.), *In Vitro Cell, Dev. Biol.*, vol. 29P:166–173, (1993).
Trolinder et al., "Genotype Specificity Of The Somatic Embryogenesis Response In Cotton", *Plant Cell Reports*, vol. 8:133–136, (1989).
Trolinder et al., "In Vitro Selection And Regeneration Of Cotton Resistant To High Temperature Stress", *Plant Cell Reports*, vol. 10:448–452, (1991).
Kado, "Molecular Mechanisms Of Crown Gall Tumorigenesis", *Critical Reviews In Plant Sciences*, vol. 10(1):1–32, (1991).
"A Simple And General Method For Transferring Genes Into Plants", *Science American Association For The Advancement of Science*, vol. 227:1229–1231, (1985).
Barrett et al. Plant Cell Tissue and Organ Culture. 1997. vol. 47: 135–144.
Carvalho et al. The EMBO Journal. 1992. vol. 11: 2595–2602.
Umbeck et al. Bio/Technology. 1987. vol. 5: 263–266.
Firoozabady and Deboer. 1993. In Vitro Cellular and Developmental Biology. vol. 29p: 166–173.
Potrykus. Ann. Rev. Plant. Physiol. 1991. vol. 42: 205–225.

*Primary Examiner*—Lynette R. F. Smith
*Assistant Examiner*—Ousama Zaghmont
*Attorney, Agent, or Firm*—Foley & Lardner

[57] ABSTRACT

A method for in vitro regeneration of fertile Gossypium plants is provided in which cells from the transition region tissue of seedlings is excised and cultured. The transition region tissue of cotton seedlings extends from the uppermost portion of the root and into the hypocotyl region. Transformed cells are regenerated into homogeneously transformed plants by means of somatic embryogenesis on hormone-free medium. A method for production of transgenic Gossypium plants capable of transmitting a foreign gene to progeny is also described in which cells derived from the transition region tissue of seedlings are targeted for transformation. The method increases the number of different cotton genotypes that can be used to make stably transformed plants capable of transmitting the foreign gene to progeny.

15 Claims, 1 Drawing Sheet

TRANSFORMATION AND REGENERATION OF FERTILE COTTON PLANTS

This application claims priority the benefit of U.S. provisional Application Ser. No. 60/028,559 filed Oct. 10, 1996 and U.S. provisional Application Ser. No. 60/029,493 filed Oct. 31, 1996.

FIELD OF THE INVENTION

This invention relates to a method for production of fertile stably transformed Gossypium plants of diverse genetic background. The transition region of seedlings is targeted for transformation with foreign DNA. Transformed plant cells are regenerated into plants by somatic embryogenesis on hormone-free medium. This invention also relates to a method for in vitro regeneration of Gossypium plants, wherein the transition region of a seedling is excised and optionally cultured in hormone-free medium.

BACKGROUND OF THE INVENTION

Production of transgenic plants requires transformation of plant cells with foreign DNA and regeneration of transgenic plants from the transformed cells. Numerous methods for transformation of plant cells are known including Agrobacterium-mediated transformation, particle gun bombardment, silicon carbide whiskers, sonication or electroporation. However, successful regeneration of plants capable of transmitting foreign DNA to progeny from the transformed cells has proven difficult for numerous economically important crops.

Microparticle-mediated transformation of cotton embryos gave rise to a very low frequency of germline transformants. See PCT/US92/01721. Bombardment of meristems produced one clonal transgenic plant per 100 to 500 meristems targeted for transformation. Only 0.1 to 1% of these transformants were capable of transmitting foreign DNA to progeny. Likewise, U.S. Pat. Nos. 5,004,863 and 5,159,135 describe a method for Agrobacterium-mediated transformation of cotton that is genotype-dependent. These patent disclosures describe successful transformation of a limited number of genotypes within *Gossypium hirsutum*.

Somatic embryogenesis has been found to be genotype dependent in many different crop species. With regard to cotton, only a few varieties in each species of the commercially important *G. hirsutum* and *G. barbadense* can generally be transformed and regenerated by somatic embryogenesis. See Trolinder et al., *Plant Cell Reports* 8: 133–136 (1989) and PCT/US92/01721. Another difficulty with this approach is that growth regulators or plant hormones are required to redirect tissue differentiation. These treatments lengthen the time period required to achieve embryogenesis and may induce somaclonal variation. Trolinder et al., 1991 *Plant Cell Reports* 10: 448–52 (1991). Somaclonal variation can be eliminated or minimized if regeneration occurs in a short time period.

Likewise, in order to recover a fertile plant that is resistant to a selected biotic or abiotic agent as a result of in vitro selection, a reproducible method for regeneration of plants is required. For example, recovery of a fertile plant that is resistant to a herbicide or pathogen through in vitro selection is dependent upon a reliable method for regeneration of a plant.

A need therefore exists for a method for regeneration of plants in vitro that can be utilized with diverse genotypes. A need also exists for a method for germline transformation of plants that can be utilized with diverse genotypes. In particular, a need exists for an efficient method for transformation of cotton plants of diverse genetic backgrounds. A need also exists for an efficient method for production of transformed cotton plants capable of transmitting a foreign gene to progeny.

SUMMARY OF THE INVENTION

Accordingly, it is an object of the present invention to provide a method for regeneration of fertile plants in vitro. In particular, another object of the present invention is to provide a means of increasing the genotype independence of methods for regeneration of fertile Gossypium plants in vitro that can be undertaken with plants of diverse genetic background.

Another object of the present invention is to provide a method for production of transgenic plants wherein the target tissue for transformation is predominantly transition region tissue.

It is another object of the present invention to provide an efficient method for production of transgenic cotton plants which is generally applicable to different genotypes of *G. hirsutum*, *G. barbadense* and other Gossypium species, wherein the target tissue for transformation is predominantly transition region tissue.

Yet another object of the present invention is to provide an efficient method for production of transformed cotton plants capable of transmitting a foreign gene to progeny.

Another object of the present invention is to provide an efficient method for production of transformed cotton plants which circumvents lengthy in vitro culture thereby reducing the frequency of somaclonal variants.

These and other objects are achieved, in accordance with one embodiment of the present invention, by providing a method for in vitro regeneration of cotton plants comprising the steps of (1) germinating a seed to produce a plantlet; (2) isolating transition region tissue; and (3) regenerating a fertile cotton plant from said transition region tissue.

Yet another embodiment of the present invention is providing a method for production of a transgenic plant comprising the steps of (1) germinating a seed to produce a plantlet; (2) isolating transition region tissue; (3) introducing an expression vector into said transition region tissue; and (4) regenerating a transgenic plant from said transition region tissue.

Another embodiment of the present invention is providing a method for the production of a transgenic Gossypium plant by (1) germinating a Gossypium seed to produce a plantlet; (2) isolating transition region tissue; (3) introducing an expression vector into said transition region tissue; and (4) regenerating a transgenic Gossypium plant.

Yet another embodiment of the present invention is regeneration on hormone-free medium of transition region tissue excised from cotton seedlings.

DETAILED DESCRIPTION OF THE PREFERRED EMBODIMENTS

1. Definitions

Figure 1:
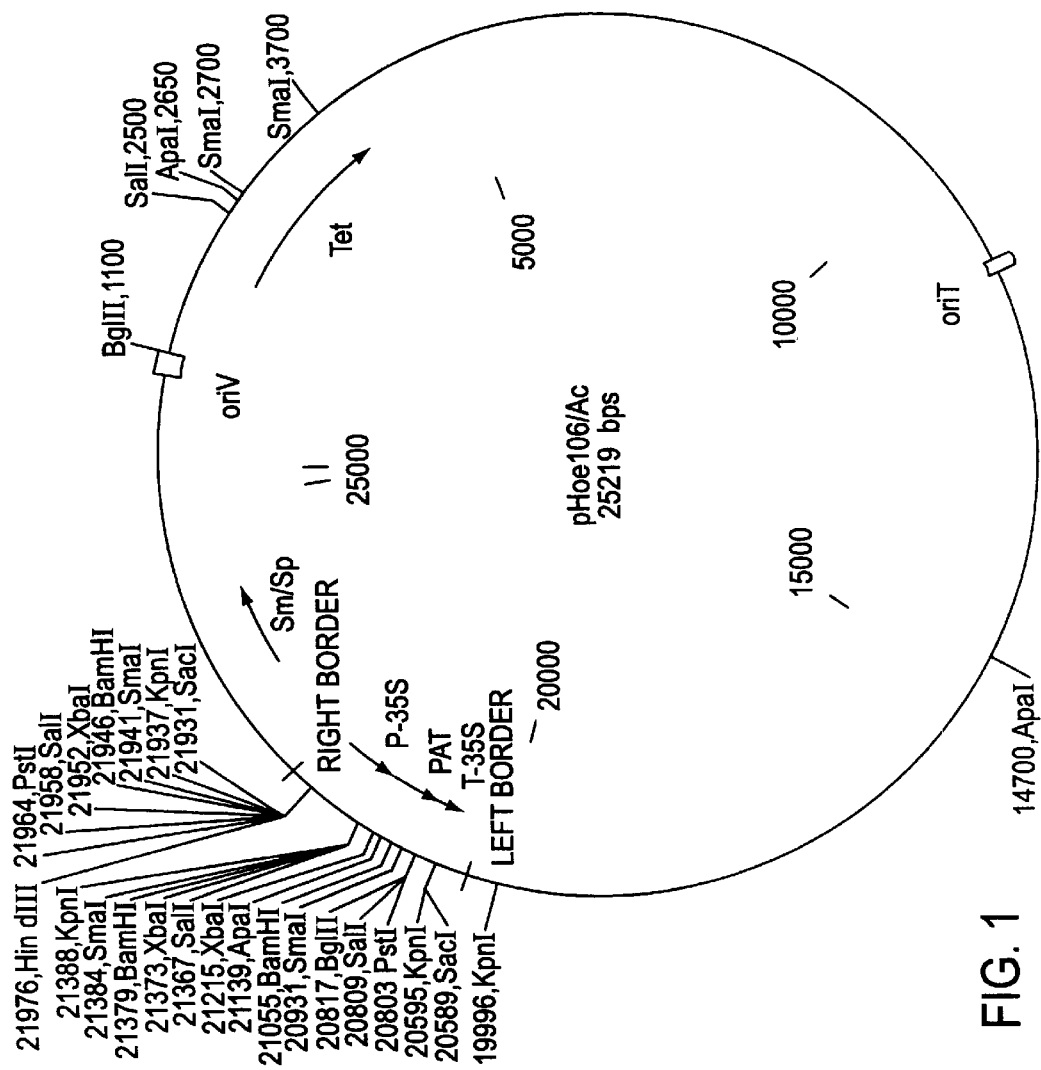
FIG. 1 presents a map of plasmid pHoe106/AC.

In the description that follows, a number of terms are used extensively. The following definitions are provided to facilitate understanding of the invention.

A structural gene is a DNA sequence that is transcribed into messenger RNA (mRNA) which is then translated into a sequence of amino acids characteristic of a specific polypeptide.

A foreign gene is any gene that has been isolated from an organism and introduced into the same organism, or another type of organism, by transformation or other recombinant methods.

An isolated DNA molecule is a DNA that is not integrated in the genomic DNA of an organism.

The term expression refers to the biosynthesis of a gene product. For example, in the case of a structural gene, expression involves transcription of the structural gene into mRNA and the translation of mRNA into one or more polypeptides.

A cloning vector is a DNA molecule, such as a plasmid, cosmid, or bacteriophage, that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance.

An expression vector is a DNA molecule comprising a gene that is expressed in a host cell. Typically, gene expression is placed under the control of certain regulatory elements, including constitutive or inducible promoters, polyadenylation sequences, tissue-specific regulatory elements, and enhancers. Such a gene is said to be operably linked to the regulatory elements.

A recombinant host may be any prokaryotic or eukaryotic cell that contains a foreign gene, cloning vector or expression vector. This term also includes those prokaryotic or eukaryotic cells that have been genetically engineered to contain the cloned gene(s) in the chromosome or genome of the host cell.

A promoter is a DNA sequence that directs the transcription of a structural gene. Typically, a promoter is located in the 5-prime region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter. For example, a promoter may be regulated in a tissue-specific or tissue-preferred manner such that it is only active in transcribing the associated coding region in a specific tissue type(s) such as leaves, roots or meristem.

Transformation includes introduction of genetic material into plant or bacterial cells. In bacterial cells the foreign DNA can reside as an autonomous replicating molecule. In plant cells, transformation results in chromosomal integration and stable heritability through meiosis.

A transqenic plant is a plant having one or more plant cells that express a foreign gene.

A transition region tissue of a seedling is where the vascular system of the root and shoot change patterns. Generally in cotton seedlings, separation between the vascular pattern of the root and shoot occurs in a region that extends from a portion of the root to just below the cotyledons. A detailed anatomical description of the cotton transition region is provided in A. M. Spieth, *Botanical Gazette* 95: 338–347 (1933), which is incorporated herein by reference. When cotton seed is germinated in vitro, the demarcation between root and shoot can be visually observed as a transition from the white root to a light green area. Therefore, in the present invention, the transition region tissue is taken from plantlets approximately 2 to 12 days post-emergence. A section measuring about 0.5 cm is carefully excised from the seedling. The section may be excised under a dissecting microscope. This section encompasses the region of the seedling where the vascular system of root becomes that of the hypocotyl. The root portion of the excised transition region contains exarch stele. The size of the root portion included in the transition region explant is optimized for each cotton cultivar. Generally, the root portion should be as small as possible because phenolics produced by the dying root tissue inhibit regeneration of the transition region into a plant in vitro. The optimum age for excision of the cotton transition region for transformation/ embryogenesis is usually about 2–12 days after radical emergence. The approximately 0.5 cm. transition region tissue which is excised from the seedling is the explant tissue that is the target for transformation in the present method.

2. Overview

The method of the present invention can be used to regenerate fertile cotton plants in vitro. Following in vitro selection of plant cells capable of growth in the presence of an abiotic or biotic agent, fertile plants are regenerated. The method of the present invention increases the number of different cotton genotypes that can be transformed. The transition region tissue excised from germinating cotton seedlings is regenerated in vitro.

The method of the present invention is also used to produce stably transformed cotton plants capable of transmitting a foreign gene to progeny. Somatic embryos are made from the transition region tissue excised from germinating Gossypium seedlings. Germline transformation applies when the germline layer, or L2 layer, of the somatic embryo is targeted for transformation with a foreign gene by biological or direct methods. Alternatively, the transition region tissue is transformed at high efficiency and then somatic embryogenesis is induced to recover fertile, stably transformed plants. The transgenic plant is capable of transmitting the foreign gene to progeny. The method of the present invention can be used to produce transgenic plants in diverse genetic backgrounds including varieties of *G. hirsutum* and *G. barbadense*.

The method of the present invention is used to produce Gossypium plants from cotton germplasm known to be recalcitrant to somatic embryogenesis. The method of the present invention permits direct transformation of elite cotton lines thereby circumventing the need for backcrossing to introduce the foreign gene into agronomically acceptable germplasm.

In addition, the present invention provides a means of avoiding prolonged in vitro culture. The transformed transition region tissue can be directly regenerated on hormone-free medium. The frequency of somaclonal variants is decreased because the in vitro culture time is reduced by this method.

It is known that a developing seedling undergoes a gradient of developmental patterns. In the developing seedling there is a transition region where the vascular system of the root and shoot change patterns. See Mauseth, The Root-Shoot Interface, in *Plant Anatomy*, Andrew Crowley and Robin Williams (eds.), The Benjamin/Cummings Publishing Company, Inc., Menlo Park, Calif. p. 289 (1988). In the transition region hormonal gradients converge. In this region there is a transition from the tetrarch and exarch vascular pattern of the primary root to the endarch pattern of the shoot. The complete transition from tetrarch to endarch may encompass all or part of the hypocotyl region in a given species. In a 4-day-old cotton seedling, for example, the transition from tetrarch to endarch begins about 1 cm below the soil level. The change in vascular pattern in successive levels of the transition region is gradual and therefore constitutes a gradient of differentiation. Generally in cotton seedlings, separation between the vascular pattern of the root and shoot occurs in a region that extends from a portion of the root to just below the cotyledons. See A. M. Spieth, *Botanical Gazette* 95: 338–347 (1933).

The establishment of polarized hormone concentration gradients in tissues are developed by localized synthesis of the hormone, translocation, and degradation. The auxin indole acetic acid (IAA) is produced mainly in growing tips, expanding leaves, and other meristematically active tissues. Although auxins are continuously produced in these tissues and translocated primarily basipetally, they do not accumulate in large amounts due to degradation. Nor do they move with unvarying speed and intensity. Polar movement of IAA is not apparent until 3 days after germination of bean and does not have full polar movement until 8 days after germination. At 8 days, the sections nearest the shoot root transition at the hypocotyl base moves progressively less IAA basipetally. See Jacobs, W. P., Amer. J. Bot. 37: 248–254 (1950). Leopold et al., *Physiol. Plant.*, 15: 631–638 (1962) reported a declining gradient of basipetal auxin transport down the stem of sunflower seedlings and Scott and Briggs, *Amer. J. Bot.*, 47: 492–499 (1960) found both extractable and diffusible auxin to decline similarly in pea. Thus, not only are there anatomical differences between different sections of the hypocotyl but there are also temporal hormonal differences. The gradient of hormones converging in the transition region might have profound effects upon the developmental fate of cells within that region.

Briefly, in one aspect, the invention comprises a series of steps wherein plant cells in a transition region explant is cultured in vitro to regenerate a fertile whole plant. In another aspect, the invention comprises a series of steps wherein plant cells in the transition region are targeted for transformation with a foreign gene. The transformed cells from the transition region are regenerated into transgenic plants capable of transmitting the foreign gene to progeny by means of somatic embryogenesis. The transition region from any plant can be targeted for transformation. A particularly preferred plant is a species of Gossypium. Most preferred plants for transformation by the methods of the instant invention are varieties of *G. hirsutum* or *G. barbadense*.

Generally, a seed of the plant to be transformed is germinated. The transition region tissue of the seedling is identified using a stereomicroscope by means of changes in vascular tissue organization and the presence of chlorophyll in cells of the hypocotyl. The age of the seedling can vary depending on the ease with which the transition region tissue can be identified for excision and transformation and regeneration into whole plants.

Transformation of the excised transition region tissue is by any known plant transformation method. In a preferred embodiment, transformation is by Agrobacterium-mediated transformation. In another embodiment, the seed is sterilized before germination. In a preferred embodiment, the seed is sterilized by a combination of sterilization procedures, i.e., Chlorox treatment followed by sonication. In yet another preferred embodiment, prior to plating out for germination, the seed is further treated in hot water to promote seed germination. The seeds are treated with hot water, generally for a time less than or equal to approximately 20 minutes, at a temperature of ranging from about 40° C. to 48° C. In a particularly preferred embodiment, heat treatment of *G. hirsutum* seed is at 48° C. for 20 minutes.

In another embodiment of the invention, tissue is excised from a plantlet grown from the seed, as described above. In a preferred embodiment, the tissue—i.e. the explant—is excised from a cotton plantlet at about 2 to 12 days post-germination of the seed. In a particularly preferred embodiment, the cotton plantlet is harvested at about 2–12 days post-germination of the seed.

In cotton, the transition region tissue excised for transformation generally constitutes the region spanning from the uppermost portion of the root into the hypocotyl and measures approximately 0.5 cm in length. However, the size of the transition region explant is generally optimized for each genotype. The root portion of the explant is typically small since phenolics and other compounds produced by damaged root tissue may inhibit subsequent growth and regeneration of the transformed explant.

Generally, sterilization of the seed, for example, cotton seed, can be accomplished as follows. Seeds (e.g., approximately 200 seeds) are placed in an open petri dish and this dish is floated on a solution of pure Chlorox in a small plastic container. The container is sealed and the seeds are gassed overnight. The following morning the petri dish and seeds are removed from the container and placed into a sterile 250 ml flask containing 100 ml of sterile water. The flask is placed in a water bath and heated to 48° C. for 20 minutes. The seeds are then allowed to imbibe for approximately two hours. The seeds are rinsed once with sterile water and placed into a small sterile beaker containing an over-the-counter solution of 3% hydrogen peroxide. The beaker containing the seeds is covered with sterile foil and placed in a small sonicator, for example, a jewelry cleaner such as the Lasonic model from Connoisseurs, and sonicated for about 15 minutes. Finally, the seeds are rinsed about 4 times with excess sterile water.

Skilled artisans readily will appreciate other acceptable seed sterilization techniques. With regard to seed lots that are highly contaminated with microorganisms, for example that has been weathered in the field prior to harvest, particularly stringent sterilization conditions may be required. For example, mercuric chloride can be used to sterilize weathered seed.

Seed sterilization of the present invention is important because (1) the hot water treatment provides for more uniform germination and conditioning of the explant, (2) Chlorox treatment alone does not sufficiently kill fungi, and (3) sonication produces cavitation which provides better access for Agrobacterium or exogenous DNA to internal tissues thereby enhancing transformation frequency. Imbibition stimulates fungal hyphal growth and the subsequent treatment with hydrogen peroxide and sonication very effectively kills or contains the fungal growth. The seed sterilization method of the present invention is important when one is working with many different cotton cultivars that exhibit different levels of seed contamination with microorganisms. The methods of the present invention provide an alternative to the use of expensive fungicides and antibiotics in the germination process. These compounds also can have deleterious effects on transformation frequency.

Approximately 2 to 12 days after radical emergence, an explant from the transition region of the seedling measuring about 0.5 cm is excised. The excised section from the seedling spans the uppermost portion of the root and beginning of hypocotyl and therefore constitutes the primary transition region. The transition region sections are placed in a petri dish containing a very small amount of water to maintain moisture until all explants have been excised. The excised explants are regenerated in vitro on hormone-free medium into fertile whole plants.

In another aspect of the invention, the explants are transformed with a foreign gene. Transformation is accomplished by any known technique and most preferably by Agrobacterium-mediated techniques. For transformation with Agrobacterium the explants are pretreated with nopaline or octopine.

In another aspect of the invention, the transformed explant is regenerated into a uniformly transgenic plant capable of transmitting a foreign gene to progeny. In a particularly preferred embodiment, the culture medium utilized for transformation does not contain plant hormones. In another preferred embodiment, if the expression vector utilized for transformation carries a selection marker gene, then the transformed explant is allowed to recover for a few days following transformation and then transferred to fresh medium containing the selective agent.

Culture media useful for somatic embryogenesis of transformed transition region tissue and regeneration of plants includes Murashige and Skoog basal salts supplemented with Gamborg's B5 vitamins, 100 µg/ml myoinositol, 30 g/l glucose and 2 to 2.5 g gelrite. Particularly preferred media for culture and regeneration of cotton include Murashige and Skoog basal salts supplemented with Gamborg's B5 vitamins, 100 µg/ml myoinositol, 30 g/l glucose, 1.9 g/l $KNO_3$ and 2 to 2.5 g gelrite (MSK). Murashige, T. and Skoog, F. *Physiol. Plant* 15: 473–497 (1962) and Gamborg et al., *Exp Cell. Res.* 50: 151–158 (1968).

Presumptively transformed plants are analyzed for expression of the foreign gene or genes using methods well known to the skilled artisan including polymerase chain reaction, Northern blot, Southern blot, ELISA, or Western blot analysis. See, for example, Sambrook et al., MOLECULAR CLONING: A LABORATORY MANUAL, Second Edition, (Cold Spring Harbor Laboratory Press, Cold Spring Harbor, N.Y. 1989).

In another aspect of the invention, the transformed plant is crossed with non-transformed in order to introgress the foreign gene into a new genetic background. Alternatively, the transformed plant is "selfed", i.e., self pollinated, in order to produce progeny that are homozygous for the foreign gene. In addition, a first transgenic plant can be crossed with a second transgenic plant to produce progeny that carry more than one foreign gene. Methods for breeding of cotton are well known to the skilled artisan. Hybridization is the most common breeding procedure for producing new cotton varieties. These procedures are similar to those used with other self-pollinated crops. See, for example, Poehlman, J. M., "Breeding Field Crops" in Van Nostrand Reinhold, 3rd Eds. (1987).

3. Methods for In Vitro Selection

Selection of plant cells for desirable characteristic in vitro is well known. See, for example Dixon, R. A. and R. A. Gonzales (eds.), PLANT CELL CULTURE, IRL Press (1994). Plant cells have been selected for resistance or tolerance to abiotic factors such as inhibitors, cold or salt. Maliga, P., *Annu. Rev. Plant Physiol.* 35: 519 (1984), Blum, A. PLANT BREEDING FOR STRESS ENVIRONMENTS, CRC Press Inc. (1988) and Freytag et al., *Plant Cell Rep.* 8: 647 (1990). Likewise, plant cells have been selected for resistance or tolerance to biotic factors such as fungal pathogens. Frame et al., Physiol. Mol. Plant Pathol., 39: 325 (1991)

4. Methods for Plant Transformation

Numerous methods for plant transformation have been developed. See, for example, Miki et al., "Procedures for Introducing Foreign DNA into Plants" in *Methods in Plant Molecular Biology and Biotechnology,* Glick, B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology,* Glick, B. R. and Thompson, J. E. Eds. (CRC Press, Inc., Boca Raton, 1993) pages 89–119.

A. Agrobacterium-mediated Transformation

The most widely utilized method for introducing an expression vector into plants is based on the natural transformation system of Agrobacterium. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes,* respectively, carry genes responsible for genetic transformation of the plant. See, for example, Kado, C.I., *Crit. Rev. Plant. Sci.* 10: 1 (1991). Descriptions of Agrobacterium vector systems and methods for Agrobacterium-mediated gene transfer are provided by Gruber et al., supra, Miki et al., supra, and Moloney et al., *Plant Cell Reports* 8: 238 (1989).

B. Direct Gene Transfer

Several methods of plant transformation, collectively referred to as direct gene transfer, have been developed as an alternative to Agrobacterium-mediated transformation.

A generally applicable method of plant transformation is microprojectile-mediated transformation wherein DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5: 27 (1987), Sanford, J. C., *Trends Biotech.* 6: 299 (1988) Sanford, J. C., *Physiol. Plant* 79: 206 (1990), Klein et al., *Biotechnology* 10: 268 (1992).

Another method for physical delivery of DNA to plants is sonication of target cells. Zhang et al. , *Bio/Technology* 9: 996 (1991). Alternatively, liposome or spheroplast fusion have been used to introduce expression vectors into plants. Deshayes et al., *EMBO J.,* 4: 2731 (1985), Christou et al., *Proc Natl. Acad. Sci. U.S.A.* 84: 3962 (1987). Direct uptake of DNA into protoplasts using $CaCl_2$ precipitation, polyvinyl alcohol or poly-L-ornithine have also been reported. Hain et al., *Mol. Gen. Genet.* 199: 161 (1985) and Draper et al. , *Plant Cell Physiol.* 23: 451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4: 1495–1505 (1992) and Spencer et al., *Plant Mol. Biol.* 24: 51–61 (1994).

Yet another technology for production of transgenic plants is whisker-mediated transformation whereby certain materials, when incubated with plant tissue, facilitates entry of DNA molecules into plant cells. It has been proposed that such materials that promote DNA uptake, primarily silicone carbide, do so by damaging the cell surface. For a review, see Wang et al., *In Vitro Cell. Dev. Biol.* 34: 101–4 (1995).

5. The Expression Vector

According to one embodiment of the present invention an expression vector is introduced into the transition region tissue of germinated Gossypium seedlings. Such an expression vector can be a previously made construct or it can be constructed from known DNA sequences by genetic engineering methods well known to one skilled in the art. The nucleotide sequence of the foreign gene can be optimized for expression in plants by modifying the codon usage to include plant preferred codons. See, for example, Murray et al., *NAR* 17: 477 (1989). Generally, such an expression vector comprises a gene that can serve as a selectable or screenable marker for transformation. In addition, the expression vector comprises a gene sequence that confers a desired trait to a transgenic plant.

According to one embodiment of the present invention, it is desired to express the foreign or agronomic genes. Accordingly, these genes are operably linked to promoters active in cotton such as the CaMV 35S, nopaline or octopine synthase promoters. See Vontling et al., *Mol. Plant-Microbe Interactions* 4(4): 370–378 (1991). Any other plant promoter active in cotton can be used including inducible, tissue-specific, tissue-preferred or constitutive promoters such as the promoters described supra. A plant gene further requires regulatory sequences such as transcription termination sequences, polyadenylation sequences, and possibly exons. Depending on the desired function of the gene, secretion or cellular compartmentalization sequences are added. All those embodiments are within the scope of the invention. The construction details will depend on the circumstances. The methods of DNA manipulation involved are standard, and well known to one skilled in the art. For an example of a handbook covering many of the techniques, see Ausubel et al. (eds.), CURRENT PROTOCOLS IN MOLECULAR BIOLOGY, (Wiley Interscience 1990).

A. Selectable or Screenable Marker Genes

Expression vectors include at least one genetic marker that allows transformed cells to be either recovered by negative selection, i.e. inhibiting growth of cells that do not contain the selectable marker gene, or by screening for product encoded by the genetic marker. Many of the commonly used selectable marker genes for plant transformation were isolated from bacteria and code for enzymes that metabolically detoxify a selective chemical agent which may be an antibiotic or a herbicide. Other selectable marker genes encode an altered target which is insensitive to the inhibitor.

The most commonly used selectable marker gene for plant transformation is the neomycin phosphotransferase II (nptII) gene, isolated from Tn5, which when placed under the control of plant regulatory signals confers resistance to kanamycin. Fraley et al., *Proc. Natl. Acad. Sci. U.S.A.*, 80: 4803 (1983). Another commonly used selectable marker gene is the hygromycin phosphotransferase gene which confers resistance to the antibiotic hygromycin. Vanden Elzen et al., *Plant Mol. Biol.*, 5: 299 (1985).

Additional selectable marker genes of bacterial origin that confer resistance to antibiotics include gentamicin acetyl transferase, streptomycin phosphotransferase, aminoglycoside-3'-adenyl transferase, and the bleomycin resistance determinant. Hayford et al., *Plant Physiol.*, 86: 1216 (1988), Jones et al., *Mol. Gen. Genet.*, 210: 86 (1987), Svab et al., *Plant Mol. Biol.* 14: 197 (1990), Hille et al., *Plant Mol. Biol.* 7: 171 (1986). Other selectable marker gene confer resistance to herbicides such as glyphosate, glufosinate, broxymil, or tabtoxine β-lactam. Comai et al., *Nature* 317: 741–744 (1985), Gordon-Kamm et al., *Plant Cell* 2: 603–618 (1990) and Stalker et al., *Science* 242: 419–423 (1988).

Selectable marker genes that are not of bacterial origin are also available. These genes include, for example, mouse dihydrofolate reductase, plant 5-enolpyruvylshikimate-3-phosphate synthase and plant acetolactate synthase. Eichholtz et al., *Somatic Cell Mol Genet.* 13: 67 (1987), Shah et al., *Science* 233: 478 (1986) and Charest et al., *Plant Cell Rep.* 8: 643 (1990).

Another class of marker genes for plant transformation require screening of presumptively transformed plant cells rather than direct genetic selection of transformed cells for resistance to a toxic substance such as an antibiotic. Commonly used genes for screening presumptively transformed cells include beta-glucuronidase (GUS), beta-galactosidase, luciferase and chloramphenicol acetytransferase. Jefferson R. A., *Plant Mol. Biol. Rep.* 5: 387 (1987), Teeri et al., *EMBO J.* 8: 343 (1989), Koncz et al., *Proc. Natl. Acad. Sci. U.S.A.* 84: 131 (1987) and De Block et al., *EMBO J.* 3: 1681 (1984).

B. Foreign Genes and Agronomic Genes

The transformation and selection techniques described above yield a transgenic plant comprising a foreign gene which can confer a trait of interest. If the gene product requires isolation, it can be extracted from a tissue of interest or from total biomass. Protein extraction from plant biomass can be accomplished by known methods, for example, as discussed by Heney and Orr, *Anal. Biochem.* 114: 92–6 (1981).

Among useful traits, the foreign gene may confer resistance to pests or disease or plants that are resistant to specific pathogen strains. See, for example Geiser et al., *Gene* 48: 109 (1986) (a *Bacillus thuringiensis* protein, a derivative thereof or a synthetic polypeptide modeled thereon). For a review of Bt δ-endotoxin genes see Kelly, et al., *Pesticide-Producing Bacteria,* in Molec. Biol. and Biotech., ed. Meyers, VCH Publishers, New-York, pages 668–72 (1995).

The foreign gene can be an enzyme inhibitor, for example, a protease or an amylase inhibitor. See, for example, Abe et al., *J. Biol. Chem.* 262: 16793 (1987) (nucleotide sequence of rice cysteine proteinase inhibitor), Huub et al., *Plant Molec. Biol.* 21: 985 (1993) (nucleotide sequence of CDNA encoding tobacco proteinase inhibitor I), and Sumitani et al., *Biosci. Biotech. Biochem.* 57: 1243 (1993) (nucleotide sequence of *Streptomyces nitrosporeus* α-amylase inhibitor). The foreign gene can also be an insect-specific hormone or pheromone such as an ecdysteroid and juvenile hormone, a variant thereof, a mimetic based thereon, or an antagonist or agonist thereof. See, for example, the disclosure by Hammock et al., *Nature* 344: 458 (1990), of baculovirus expression of a cloned juvenile hormone esterase, an inactivator of juvenile hormone. The foreign gene can be an insect-specific peptide or neuropeptide which, upon expression, disrupts the physiology of the affected pest. For example, see the disclosures of Regan, *J. Biol. Chem.* 269: 9 (1994) (expression cloning yields DNA coding for insect diuretic hormone receptor), and Pratt et al., *Biochem. Biophys. Res. Comm.* 163: 1243 (1989) (an allostatin is identified in *Diploptera puntata*).

The foreign gene may be an insect-specific venom produced in nature by a snake, a wasp, etc. For example, see Pang et al., *Gene* 116: 165 (1992), for disclosure of heterologous expression in plants of a gene coding for a scorpion insectotoxic peptide. The foreign gene can provide insecticidal activity by producing an hyperaccumulation of a monterpene, a sesquiterpene, a steroid, hydroxamic acid, a phenylpropanoid derivative or another non-protein molecule with insecticidal activity. Alternatively, the foreign gene can provide insecticidal activity by expressing an enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. DNA molecules which contain chitinase-encoding sequences can be obtained, for example, from the ATCC under accession Nos. 39637 and 67152. See also Kramer et al., *Insect Biochem. Molec. Biol.* 23: 691 (1993), who teach the nucleotide sequence of a cDNA encoding tobacco hookworm chitinase, and Kawalleck et al., *Plant Molec. Biol.* 21: 673 (1993), who provide the nucleotide sequence of the parsley ubi4-2 polyubiquitin gene.

Furthermore, the foreign protein can be a viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

It may be desirable to express the foreign gene in a plant to confer resistance to a herbicide such as glyphosate (resistance imparted by mutant EPSP synthase) and other phosphono compounds such as glufosinate (PAT and bar genes), and pyridinoxy or phenoxy proprionic acids and cyclohexones (ACCase inhibitor-encoding genes). See, for example, U.S. Pat. No. 4,940,835 to Shah et al., which discloses the nucleotide sequence of a form of EPSP which can confer glyphosate resistance. European patent application No. 0 333 033 to Kumada et al. and U.S. Pat. No. 4,975,374 to Goodman et al. disclose nucleotide sequences of glutamine synthetase genes which confer resistance to herbicides such as L-phosphinothricin and Kinschenf et al., *J. Bacteriol.* 173: 4124–4132 (1991) describes a cloned DNA sequence encoding a protein that confers resistance to TBL. The nucleotide sequence of a phosphinothricin-acetyl-transferase gene is provided in European application No. 0 242 246 to Leemans et al. De Greef et al., *Bio/Technology* 7: 61 (1989), describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop, are the Acc1-S1, Acc1-S2 and Acc1-S3 genes described by Marshall et al., *Theor. Appl. Genet.* 83: 435 (1992).

The foreign gene may encode a herbicide that inhibits photosynthesis, such as a triazine (psbA and gs+ genes) and a benzonitrile (nitrilase gene). Przibilla et al., *Plant Cell* 3: 169 (1991), describe the transformation of Chlamydomonas with plasmids encoding mutant psbA genes. Nucleotide sequences for nitrilase genes are disclosed in U.S. Pat. No. 4,810,648, and DNA molecules containing these genes are available under ATCC accession Nos. 53435, 67441 and 67442. Cloning and expression of DNA coding for a glutathione S-transferase is described by Hayes et al., *Biochem. J.* 285: 173 (1992).

Furthermore, the foreign gene may enhance the value of the plant. The foreign gene may be an antisense gene that modifies fatty acid metabolism. See Knultzon et al., *Proc. Nat'l Acad Sci., USA* 89: 2624 (1992). Alternatively, the foreign gene may encode a protein that modifies the properties of cotton fiber. See, for example, PCT/US94/11121 and PCT/US93/11412. Additionally, the foreign gene can be used to engineer cotton lines that are male sterile thereby facilitating construction of cotton hybrids. A gene encoding a product which disrupts pollen development is introduced into an inbred line and used for efficient production of hybrid seed. See, for example, WO 89/10396. The transgenic plant can also be used as a bioreactor for commercial production and isolation of any desired gene product.

C. Promoters

1. Constitutive Promoters

Many different constitutive promoters can be utilized in the instant invention. Exemplary constitutive promoters include the promoters from plant viruses such as the 35S promoter from CaMV (Odell et al., *Nature* 313: 810–812 (1985) and the promoters from such genes as rice actin (McElroy et al., *Plant Cell* 2: 163–171 (1990)) or ubiquitin. Christensen et al., *Plant Mol. Biol.* 12: 619–632 (1989) and Christensen et al., *Plant Mol. Biol.* 18: 675–689 (1992).

2. Inducible Promoters

Any inducible promoter can be used in the instant invention. See Ward et al. *Plant Mol. Biol.* 22: 361–366 (1993). Exemplary inducible promoters include that from the ACE1 system which responds to copper (Mett et al. *PNAS* 90: 4567–4571 (1993)) or Tet repressor from Tn10 (Gatz et al., *Mol. Gen. Genet.* 227: 229–237 (1991). An exemplary inducible promoter that responds to an inducing agent to which plants do not normally respond is the inducible promoter from a steroid hormone gene the transcriptional activity of which is induced by a glucocorticosteroid hormone. Schena et al., *Proc. Natl. Acad. Sci. U.S.A.* 88: 10421 (1991).

The expression vector comprises an inducible promoter operably linked to a foreign gene. The expression vector is introduced into plant cells and presumptively transformed cells are exposed to an inducer of the inducible promoter. The cells are screened for the presence of the foreign protein by methods well known to the skilled artisan such as ELISA or Western blotting. See, for example, Ausubel et al., (eds.) CURRENT PROTOCOLS IN MOLECULAR BIOLOGY (Wiley Interscience 1990).

3. Tissue-Specific or Tissue-Preferred Promoters

Any tissue-specific or tissue-preferred promoter can be utilized in the instant invention. Exemplary tissue-specific or tissue-preferred promoters include a root-preferred promoter such as that from the phaseolin gene (Murai et al., *Science* 23: 476–482 (1983) and Sengupta-Gopalan et al., *Proc. Natl. Acad. Sci. USA* 82: 3320–3324 (1985)); a leaf-specific and light-induced promoter such as that from cab or rubisco (Simpson et al., *EMBO J.* 4(11): 2723–2729 (1985) and Timko et al., *Nature* 318: 579–582 (1985)) or an anther-specific promoter such as that from LAT52 (Twell et al., *Mol. Gen. Genet.* 217: 240–245 (1989).

The expression vector comprises a tissue-specific or tissue-preferred promoter operably linked to a foreign gene. The expression vector is introduced into plant cells. The cells are screened for the presence of the foreign protein.

The present invention, thus generally described, will be understood more readily by reference to the following examples, which are provided by way of illustration and are not intended to be limiting of the present invention.

EXAMPLE 1

Regeneration of Fertile *G. hirsutum* from Transition Region Tissue Excised from Seedlings Seeds from *G. hirsutum* varieties designated DPL 2156, SureGrow 501, SureGrow AZ180, SureGrow AZ96 and Paymaster HS200 were sterilized by placing approximately 200 seeds in an open petri dish. This petri dish was floated in a larger petri dish containing a solution of pure Chlorox. These dishes were placed in a small plastic container. The container was sealed and the seeds gassed overnight.

The following morning the petri dish and seeds were removed from the container and placed in a sterile 250 ml flask containing 100 ml of sterile water. The flask was placed in a water bath and heated to 48° C. for 20 minutes. The seeds were then allowed to imbibe for approximately two hours, rinsed once with sterile water and then placed into a small sterile beaker containing a 3% solution of hydrogen peroxide. The beaker containing the seeds was covered with sterile foil and placed in a small sonicator designed for cleaning jewelry and sonicated for 15 minutes. Seeds were then rinsed 4 times with excess sterile water.

Sterilized seeds were placed onto petri plates or 25×150 mm culture tubes containing Stewart and Hsu's medium supplemented with 5 g/l sucrose, 2.0 g/l gelrite and 5 g/l agar, pH 6.8, as described by Stewart, McD. J. and Hsu, C. L. *Planta* 137: 113–117 (1977), for various time periods. At selected time periods between 1 to 12 days after radical emergence, a tissue section measuring about 0.5 cm was excised from the cotton seedlings. The sections were excised from the region spanning the termination of the root and beginning of hypocotyl which is the primary transition region.

The demarcation between root and shoot was visually observed as a transition from the white root to a light green area often tinged with anthocyanin and containing glands in glanded varieties. The shoot region of the elongating hypocotyl was dark green. At this region the root area will blacken and die if excess root tissue is present when placed on basal MS medium while the shoot portion will produce callus. Accordingly, as little root tissue was excised from the transition region as possible in order to minimize the amount of phenolics that were released into the culture medium following removal of the explant from the seedling.

Excised transition regions were placed onto hormone-free MSNH medium containing 1.9 g/l $KNO_3$ (MSK). Plates were incubated for one week under low light at 30° C. After one week the explants were transferred to hormone-free MSK medium.

The explants were incubated under low light at 30° C. and transferred at five week intervals onto fresh hormone-free MSK medium until plantlets formed. Plantlets (embryos ready for germination) formed within 2.5 to 4 months following this procedure. No hormones were used at any time during in vitro culture.

The regeneration frequency expressed as a percent excised transition regions that produced plantlets was 18.6, 4.2, 2.4, 0.3 and 10.6% for Paymaster HS200, SureGrow 501, SureGrow AZ180, SureGrow AZ96, and DPL 2156, respectively. The optimum age for transition region explant excision for in vitro culture and embryogenesis according to the present invention was approximately 1–5 days after radical emergence based upon the total number of embryonic calli obtained during this time period. The optimum age varies, however, depending upon seedling vigor and genotype.

Plantlets recovered from SureGrow 501, SureGrow AZ180, SureGrow AZ96, HS200 and DPL2156 transition region explants were grown to maturity. Each of the regenerated plants was fertile and produced seeds upon selfing. Seeds produced on plants regenerated from transition zone tissue excised from SureGrow 501, SureGrow AZ180, SureGrow AZ96, HS200 and DPL2156 were tested for germination and were viable.

Attempts were made to regenerate cotton plants from transition region tissue excised from 27 other *G. hirsutum* cultivars according to the methods described herein. Some of these cultivars did not produce embryogenic callus (14), others produced embryogenic callus but the embyros did not develop beyond the globular stage (10), while the remainder produced mature embyros from which plants can be regenerated (3).

EXAMPLE 2

Introduction of Foreign DNA and Selection of TransformantS

Excised transition region sections were obtained from Paymaster HS200, SureGrow 501, SureGrow AZ180, SureGrow AZ96, and DPL 2156 as described in Example 1. These were placed in a petri dish containing a very small amount of water to maintain moisture until all explants had been excised. The explants were pretreated for 5.0 minutes with a 30 mM solution of nopaline or octopine, depending on the Agrobacterium strain to be used for transformation, dissolved in 2% DMSO and adjusted to pH 5.5 with 6N KOH.

The explants were then exposed to a ½₀ dilution of a saturated overnight culture of Agrobacterium strain LB4404 harboring plasmid pBI121. LB4404 also harbors the Ti plasmid of a non-oncogenic strain of *A. tumefaciens* for transformation. It is preferred that the Agrobacterium strain harbor a binary Ti plasmid system. Agrobacterium strain LB4404 and plasmid pBI121 are commercially available from Clontech, 1020 East Meadow Circle, Palo Alto, Calif. 94303. Plasmid pBI121 is a 13.0 kb vector based on pBI101 containing a 800 bp HindIII-BamHI fragment with the cauliflower mosaic virus (CaMV 35S) promoter operably linked to the GUS gene. In addition, plasmid pBI121 carries the NPTII transferase gene under control of the NOS promoter. Accordingly, introduction of pBI121 into plant cells confers kanamycin resistance and high levels of GUS expression.

Plasmid pBI121 was introduced into Agrobacterium strain LB4404 by triparental mating according to procedures provided by Clontech. Agrobacterium harboring plasmid pBI121 were induced for transformation of plant tissue by overnight culture in Luria Broth containing 10 micromolar acetosyringinone and 100 μg/ml streptomycin and 50 μg/ml kanamycin.

The cotton transition region tissue explants, incubated for 5.0 minutes in 30 mM nopaline as described supra, were co-cultured with a ½₀ dilution of the overnight culture of Agrobacterium LB4404(pBI121) in petri plates containing Murashige and Skoog's medium supplemented with Gamborg's B5 vitamins (MSNH). This culture medium did not contain any plant growth hormones. Plates were stored in the dark at room temperature (25° C.) for 3 days or until a distinct halo of bacteria was visible. Transition region explants were then removed from the co-cultivation plate, blotted to remove excess bacteria, and placed onto hormone-free MSNH medium containing 1.9 g/l $KNO_3$ (MSK). Plates were incubated for one week under low light at 30° C. After one week the explants were transferred to hormone-free MSK medium containing 35 ug/ml kanamycin and 500 ug/ml Claforan.

The explants were incubated in low light at 30° C. and transferred at five week intervals onto fresh hormone-free MSK medium containing 35 μug/ml kanamycin and 500 ug/ml Claforan until calli are formed. Not all transition region explants formed calli but those that did were embryogenic if the calli sustained growth beyond 9 to 12 weeks. Non-embryogenic calli became necrotic and ceased growth during that period. No hormones were used at any time during in vitro culture. The frequency of presumptive transformation events obtained following this method, based upon growth in the presence of kanamycin and transient assays for GUS expression, ranged from 50% to 100% of the explants. GUS assays were performed according to well-known methods. See, for example, Jefferson, R. A., *Plant Mol. Biol. Rep.* 5: 387 (1987). The transformation frequency for cotton transition region explants isolated from 5 and 12 day old seedlings was approximately 2-fold greater than for transition region explants isolated from younger cotton seedlings.

EXAMPLE 3

Transformation of Cultivar SG501 with the Pat Gene

Transition region explants were excised from seedlings of cotton cultivar SureGrow 501 3 days post-emergence according to the methods described in Example 1. Explants were placed in a petri dish with a small amount of water to maintain moisture until all explants had been excised. Explants were then rinsed three times with fresh sterile water and pretreated for 5.0 min with a solution of 30 mM nopaline in 2% DMSO adjusted to a pH 5.5 with 6N KOH.

The explants were then exposed to 1/20 dilution of a saturated overnight culture of *A. tumefaciens* strain C58 harboring the Ti-plasmid EHA101 and the binary vector pHoe106/AC. A map of plasmid pHoe106/AC is shown in FIG. 1. Plasmid pHoe106/AC is 25.2 kb in size and contains a 550 bp synthetic DNA fragment encoding the enzyme phosphinothricin acetyltransferase (PAT). The pat gene is operably linked to the promoter and terminator of the 35S gene from cauliflower mosaic virus (CaMV). PAT confers resistance to the herbicide bialaphos or glufosinate. Accordingly, transformation of plant cells with plasmid pHoe106/Ac confers resistance to herbicide glufosinate.

Transition region explants inoculated with the this Agrobacterium strain were placed onto petri dishes containing Murashige and Skoog's medium supplemented with Gamborg's B5 vitamins, 30 g/l glucose, 2 g/l gelrite, and 0.75 g/l MgC12 (MSNH) and co-cultured in the dark for 2 days or until a distinct halo of bacteria was visible. Explants were then removed from the coculture medium, blotted to remove excess bacteria, and then placed onto hormone-free MSNH medium supplemented with 1.9 g/l KNO3 (MSK) and 500 mg/l Claforan. Plates were incubated for 10 days under low light at 300° C. Following 10 days the explants were transferred to hormone-free (MSK) medium containing 500 ug/l claforan and 7.2 $\mu$M glufosinate.

Explants were incubated in low light at 30° C. and transferred at 5 week intervals onto fresh medium until calli and embryos formed. It is necessary to transfer explants periodically because the antibiotic loses effectiveness and continued selection is necessary to eliminate contamination of the cultures with Agrobacterium.

A total of 10.8% of calli generated from transition region explants were embryogenic on the selection medium. Plants were regenerated from each of the presumptively transformed embryogenic calli and tested for resistance to the herbicide. A drop of glufosinate was placed on the leaf tissue after the plantlet had obtained 5 to 6 leaves. 100% of the plants regenerated from presumptively transformed cell lines were resistant to the herbicide while non-transformed controls were sensitive. To determine whether the PAT enzyme was detectable, ELISA assays were performed on each of these herbicide resistant plants according to known methods. See, for example, PAT ELISA Kit Article No. 24016E07.FWD, Steffens Biotechnishe Analysen GmbH, Baumgartenstr. 5, D-79285 Ebingen (FRG). Each of the herbicide resistant plants also contained the PAT enzyme while no-transformed control plants did not. Accordingly, 10.8% of the calli generated from cotton transition zone explants transformed by the methods of the instant invention produced transgenic plants.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publication and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety.

What is claimed is:

1. A method for the in vitro regeneration of a Gossypium plant comprising the steps of:
    a) germinating a seed to produce a plantlet;
    b) isolating transition region tissue from said plantlet;
    c) and regenerating under hormone-free conditions a fertile Gossypium plant from said transition region tissue.

2. The method according to claim 1, wherein said Gossypium plant is *G. hirsutum*.

3. The method according to claim 1, wherein said Gossypium plant is *G. barbadense*.

4. The method according to claim 1, wherein said seed of step (a) is sterilized prior to germination.

5. The method according to claim 4, wherein said sterilization step comprises treatment of said seed with Chlorox followed by sonication.

6. The method according to claim 1, wherein said seed of step (a) is incubated in water having a temperature in the range of about 40 to 48° C. in order to increase germination efficiency.

7. A method for production of a transgenic Gossypium plant comprising the steps of:
    a) germinating a seed to produce a plantlet;
    b) isolating transition region tissue from said plantlet;
    c) introducing an expression vector into said transition region tissue; and
    d) regenerating under hormone-free conditions a transgenic Gossypium plant from said transition region tissue.

8. The method according to claim 7, wherein said Gossypium plant is *G. hirsutum*.

9. The method according to claim 7, wherein said Gossypium plant is *G. barbadense*.

10. The method according to claim 7, wherein said seed of step (a) is sterilized prior to germination.

11. The method according to claim 10, wherein said sterilization step comprises treatment of said seed with Chlorox followed by sonication.

12. The method according to claim 7, wherein said seed of step (a) is incubated in water having a temperature in the range of about 40 to 48° C. in order to increase germination efficiency.

13. The method according to claim 7, wherein said expression vector is introduced into said explant by Agrobacterium-mediated transformation.

14. The method according to claim 7, further comprising the step of selfing said transgenic plant to produce homozygous transgenic progeny.

15. The method according to claim 7, further comprising the step of crossing said transgenic plant with a second plant in order to introgress said foreign DNA into a different genetic background.

* * * * *